(12) United States Patent
Vernon

(10) Patent No.: US 10,775,107 B2
(45) Date of Patent: Sep. 15, 2020

(54) NESTED-FLOW HEAT EXCHANGERS AND CHEMICAL REACTORS

(71) Applicant: BAYOTECH, INC., Albuquerque, NM (US)

(72) Inventor: Milton E. Vernon, Albuquerque, NM (US)

(73) Assignee: BAYOTECH, INC., Albuquerque, NM (US)

( * ) Notice: Subject to any disclaimer, the term of this patent is extended or adjusted under 35 U.S.C. 154(b) by 0 days.

(21) Appl. No.: 16/672,037

(22) Filed: Nov. 1, 2019

(65) Prior Publication Data

US 2020/0132383 A1 Apr. 30, 2020

Related U.S. Application Data

(60) Continuation of application No. 16/229,474, filed on Dec. 21, 2018, now Pat. No. 10,465,990, which is a
(Continued)

(51) Int. Cl.
*F28D 7/10* (2006.01)
*F28D 7/00* (2006.01)
(Continued)

(52) U.S. Cl.
CPC .............. *F28D 7/103* (2013.01); *B01J 8/008* (2013.01); *B01J 8/0257* (2013.01); *B01J 8/0278* (2013.01);
(Continued)

(58) Field of Classification Search
CPC ....... B01J 7/00; B01J 8/00; B01J 8/008; B01J 8/02; B01J 8/0242; B01J 8/0257; B01J 8/0278; B01J 8/0285; B01J 8/04; B01J 8/0446; B01J 8/0461; B01J 8/0465; B01J 12/00; B01J 12/007; B01J 15/00; B01J 15/005; B01J 19/00–0013; B01J 19/24;
(Continued)

(56) References Cited

U.S. PATENT DOCUMENTS 5,275,632 A 1/1994 Corrigan
5,429,809 A 7/1995 Stahl
(Continued)

FOREIGN PATENT DOCUMENTS

DE 2658086 A1 9/1977
WO WO2018112104 A1 6/2018
(Continued)

*Primary Examiner* — Natasha E Young
(74) *Attorney, Agent, or Firm* — Fish & Richardson P.C.

(57) ABSTRACT

Disclosed is a technology based upon the nesting of tubes to provide chemical reactors or chemical reactors with built in heat exchanger. As a chemical reactor, the technology provides the ability to manage the temperature within a process flow for improved performance, control the location of reactions for corrosion control, or implement multiple process steps within the same piece of equipment. As a chemical reactor with built in heat exchanger, the technology can provide large surface areas per unit volume and large heat transfer coefficients. The technology can recover the thermal energy from the product flow to heat the reactant flow to the reactant temperature, significantly reducing the energy needs for accomplishment of a process.

21 Claims, 7 Drawing Sheets

Related U.S. Application Data continuation of application No. 15/934,763, filed on Mar. 23, 2018, now Pat. No. 10,401,092, which is a division of application No. 14/645,490, filed on Mar. 12, 2015, now Pat. No. 9,958,211.

(51) Int. Cl.

| | | |
|---|---|---|
| *F28D 7/12* | (2006.01) | |
| *B01J 7/00* | (2006.01) | |
| *B01J 8/00* | (2006.01) | |
| *B01J 8/02* | (2006.01) | |
| *B01J 8/04* | (2006.01) | |
| *B01J 12/00* | (2006.01) | |
| *B01J 19/00* | (2006.01) | |
| *B01J 19/24* | (2006.01) | |
| *F28F 1/12* | (2006.01) | |
| *C01C 1/04* | (2006.01) | |
| *C05C 9/00* | (2006.01) | |
| *C07C 273/04* | (2006.01) | |
| *C01B 3/38* | (2006.01) | |
| *C01B 3/48* | (2006.01) | |
| *H01M 8/06* | (2016.01) | |
| *H01M 8/0612* | (2016.01) | |
| *F28D 21/00* | (2006.01) | |

(52) U.S. Cl.
CPC .......... *B01J 8/0285* (2013.01); *B01J 8/0465* (2013.01); *B01J 12/007* (2013.01); *C01B 3/384* (2013.01); *C01B 3/48* (2013.01); *C05C 9/00* (2013.01); *C07C 273/04* (2013.01); *F28D 7/12* (2013.01); *F28F 1/122* (2013.01); *H01M 8/0618* (2013.01); *B01J 2208/0053* (2013.01); *B01J 2208/00212* (2013.01); *B01J 2208/00309* (2013.01); *B01J 2208/025* (2013.01); *B01J 2219/0072* (2013.01); *B01J 2219/00495* (2013.01); *B01J 2219/00745* (2013.01); *C01B 2203/0233* (2013.01); *C01B 2203/0283* (2013.01); *C01B 2203/068* (2013.01); *C01B 2203/0811* (2013.01); *C01B 2203/1241* (2013.01); *C01B 2203/82* (2013.01); *F28D 2021/0022* (2013.01); *H01M 2250/10* (2013.01); *Y02B 90/14* (2013.01); *Y02P 20/124* (2015.11); *Y02P 20/142* (2015.11); *Y02P 20/52* (2015.11)

(58) Field of Classification Search
CPC .......... B01J 2208/00; B01J 2208/00008; B01J 2208/00017; B01J 2208/00106; B01J 2208/00168; B01J 2208/00212; B01J 2208/00309; B01J 2208/0053; B01J 2208/02; B01J 2208/023; B01J 2208/024; B01J 2208/025; B01J 2219/00049; B01J 2219/00051; B01J 2219/00074; B01J 2219/00117; B01J 2219/00274; B01J 2219/00277; B01J 2219/00495; B01J 2219/00718; B01J 2219/0072; B01J 2219/00745; C01B 3/00; C01B 3/02; C01B 3/32; C01B 3/34; C01B 3/38; C01B 3/384; C01B 3/48; C01B 2203/00–0205; C01B 2203/0227; C01B 2203/0233; C01B 2203/0283; C01B 2203/06; C01B 2203/068; C01B 2203/08–0811; C01B 2203/12–1211; C01B 2203/1235; C01B 2203/1241; C01B 2203/80; C01B 2203/82; C01C 1/00; C01C 1/02; C01C 1/04; C01C 1/0405; C01C 1/0417; C01C 1/0482; C05C 9/00; C07C 273/00; C07C 273/02; C07C 273/04; F28D 7/00; F28D 7/10; F28D 7/103; F28D 7/12; F28D 21/00; F28D 2021/0019; F28D 2021/002; F28F 1/00; F28F 1/10; F28F 1/12; F28F 1/122; H01M 8/00; H01M 8/06–0618; H01M 2250/10; Y02B 90/10; Y02B 90/14; Y02P 20/10–122; Y02P 20/124; Y02P 20/14–142; Y02P 20/50
See application file for complete search history.

(56) References Cited

U.S. PATENT DOCUMENTS

| | | |
|---|---|---|
| 5,639,431 A | 6/1997 | Shirasaki |
| 5,876,469 A | 3/1999 | Moriya |
| 6,206,090 B1 | 3/2001 | Rago |
| 6,958,135 B1 | 10/2005 | Filippi |
| 6,977,064 B1 | 12/2005 | Adris |
| 7,195,742 B2 | 3/2007 | Liu |
| 7,501,102 B2 | 3/2009 | Whittenberger |
| 7,517,373 B2 | 4/2009 | Sakai |
| 7,517,507 B2 | 4/2009 | Kuwabara |
| 7,601,304 B1 | 10/2009 | Palmas |
| 7,645,437 B1 | 1/2010 | Moore |
| 7,749,290 B2 | 7/2010 | Wallace |
| 7,780,926 B2 | 8/2010 | Boe |
| 7,867,460 B2 | 1/2011 | Singh |
| 7,871,593 B2 | 1/2011 | Erkes |
| 7,972,572 B2 | 7/2011 | Fusselman |
| 8,057,559 B2 | 11/2011 | Ichikawa |
| 8,114,173 B2 | 2/2012 | Lee |
| 8,273,314 B2 | 9/2012 | Fischer |
| 8,303,163 B2 | 11/2012 | Schneider |
| 8,337,573 B2 | 12/2012 | Neels |
| 8,597,595 B2 | 12/2013 | Akin |
| 8,721,747 B2 | 5/2014 | Sprouse |
| 8,747,496 B2 | 6/2014 | Neels |
| 9,149,773 B2 | 10/2015 | Brosten |
| 9,149,781 B2 | 10/2015 | Schrauwen |
| 9,228,740 B2 | 1/2016 | Stevenson |
| 9,308,510 B2 | 4/2016 | Hazeltine |
| 9,309,473 B2 | 4/2016 | McAlister |
| 9,403,738 B2 | 8/2016 | Skowerski |
| 9,433,909 B2 | 9/2016 | Vetter |
| 9,791,074 B2 | 10/2017 | Hoglund |
| 9,958,211 B2 | 5/2018 | Vernon |
| 10,401,091 B2 | 9/2019 | Vernon |
| 10,401,092 B2 | 9/2019 | Vernon |
| 10,465,990 B2 | 11/2019 | Vernon |
| 2011/0318660 A1 | 12/2011 | Mukai |
| 2013/0312946 A1* | 11/2013 | Chan ..................... F28D 7/005 165/281 |
| 2016/0282052 A1 | 9/2016 | Vernon |
| 2017/0021324 A1 | 1/2017 | Blanchet |
| 2018/0086637 A1 | 3/2018 | Gray |
| 2018/0134629 A1 | 5/2018 | Kolios |
| 2018/0209743 A1 | 7/2018 | Vernon |
| 2018/0216893 A1 | 8/2018 | Vernon |
| 2019/0002401 A1 | 1/2019 | Scotto |
| 2019/0113284 A1 | 4/2019 | Vernon |

FOREIGN PATENT DOCUMENTS

| | | |
|---|---|---|
| WO | WO2018139920 A1 | 8/2018 |
| WO | WO2018206167 A1 | 11/2018 |
| WO | WO2019043523 A1 | 3/2019 |

* cited by examiner

NESTED-FLOW HEAT EXCHANGERS AND CHEMICAL REACTORS

CROSS-REFERENCE TO RELATED APPLICATIONS

This application is a continuation of U.S. patent application Ser. No. 16/229,474, filed Dec. 21, 2018, (now U.S. Pat. No. 10,465,990, issued Nov. 5, 2019), entitled "NESTED-FLOW HEAT EXCHANGERS AND CHEMICAL REACTORS," which is a continuation of U.S. patent application Ser. No. 15/934,763, filed Mar. 23, 2018, (now U.S. Pat. No. 10,401,092, issued Sep. 3, 2019), entitled "NESTED-FLOW HEAT EXCHANGERS AND CHEMICAL REACTORS," which is a divisional of U.S. patent application Ser. No. 14/645,490, filed Mar. 12, 2015, (now U.S. Pat. No. 9,958,211, issued May 1, 2018), entitled "NESTED-FLOW HEAT EXCHANGERS AND CHEMICAL REACTORS," of which the entire contents of each is hereby incorporated by reference herein in its entirety.

BACKGROUND OF THE INVENTION

Field of the Invention

The present invention relates to equipment for processing chemicals and other fluid cycles bases on temperature change, including power cycles. The equipment includes heat exchangers and chemical reactors. The present invention significantly reduces the capital investment required for this type of equipment through use of standard construction techniques and materials. The present invention also significant improved heat transfer performance, where needed, which significantly reduces energy consumption for product production.

Description of the Prior Art

Heat exchangers and chemical reactors are commonly used equipment in chemical processing and recuperated power cycles. This equipment is used in a broad spectrum of industries and in all stages of processing.

Heat exchangers are used to transfer heat (thermal energy) from one process flow to another. Heat exchangers come in a variety of designs, including: tube-in-shell, flat plate, tube-in-tube, spiral-flow, and recently developed bonded-etched-plates usually referred to as printed circuit heat exchangers. Heat exchanger technologies are characterized by their respective flow path hydraulic diameters and the heat transfer area per unit size. Both the hydraulic diameter and heat transfer area per size scale inversely with the hydraulic diameter, thus the total energy transferred per unit time for a fixed temperature difference scales inversely with the square of the hydraulic diameter. This means that for a fixed sized heat exchanger, if one is constructed using tubes that are one-half the tube size in the other, the one with the smaller tubes can transfer four times the energy per unit time for the same temperature difference. This has led to smaller and smaller hydraulic diameter heat exchanger until now we are constructing heat exchangers using printed circuit etching technologies. These heat exchangers use hydraulic diameters flow paths down to 0.5 mm and resulting areas per volumes of up to 1300 $m^2/m^3$ (http://www.heatric.com/typical_characteristics.html). But the construction technique for making printed circuit heat exchanger is quite complex and only a limited production capability exists, resulting in both high cost and long delivery times for these heat exchangers. Heat exchanger costs per performance determine the overall heat exchanger efficiency that one can afford to implement into a process. A higher cost heat exchanger technology limits the total heat exchanger efficiency due to the tradeoff between heat exchanger cost and replacement energy cost. A lower cost heat exchanger technology achieves a higher efficiency as a result of that same tradeoff.

Chemical reactors are used to change a fluid from one chemical species to another. Chemical reactors operate at a variety of pressures and temperatures, where these parameters are adjusted for best performance within the chemical reactors capabilities. Some chemical reactors include catalyst while others have no need for catalyst, depending upon the kinetics of the chemical reaction. Four examples of chemical reactors are presented here for prior art description: hydrogen production using the Steam Methane Reforming (SMR) process; hydrogen production using the Water Shift Reaction (WSR) process; ammonia production using the Haber-Bosch process; and urea production from carbon-dioxide and ammonia. These processes are used in commercial fertilizer production, which is one of the targets for application of this invention.

Today's SMR process involves the combustion of methane within a combustion chamber which is lined with pressurized and catalyst loaded reaction tubes in which the endothermic reaction of turning a mixture of methane and water to carbon-monoxide and hydrogen is accomplished. Although this process can be operated at low pressures, the tendency is to operate this process at 10-20 atmospheres to minimize the number of reaction tubes and subsequent pumping operations. Because this process is an endothermic reaction, it is favored at higher temperatures and usually operated at temperatures between 850° C. and 1000° C. The catalyst is used to improve the reaction kinetics (speed of conversion) also in an effort to reduce the number of reaction tubes. The energy conversion in these systems is reported to be in the low 70% levels due to several factors, these include: an additional 30% energy requirement to heat the SMR reactants from room temperature to reaction temperature as compared to the energy needs to accomplish the process at temperature; and consumption of 35% of the combustion energy to raise the combustion reactants from room temperature to SMR reaction temperature. In addition to the low energy efficiency of today's SMR process, the capital cost of the system is high due to the strength of material required for the SMR reaction tubes. These tubes are operated at high temperatures, while coupled to a low pressure source of heat; forcing their construction from expensive materials, adding significantly to the cost of the SMR system. Because the cost of natural gas is significantly higher in Europe than it is in the US, several European fertilizer production facilities have incorporated a heat exchanger to recover the SMR product flow energy and utilize it for heating up the SMR reactant flow. This energy recuperation improves one of the energy demands in this system.

Today's Water Shift Reaction (WSR) usually combines the carbon-monoxide from the SMR process and an outside source of steam to produce carbon-dioxide and hydrogen. Because of the characteristics of the WSR, the process is favored at lower temperatures, although a lower temperature bond exists due to catalyst performance. The process is slightly exothermic, and in today's systems the WSR result in a temperature rise in the process flow temperature. This temperature rise limits the WSR conversion fraction, to offset that limitation the WSR is usually conducted in two stages with cooling provided between these stages for higher conversion.

Today's Haber-Bosch process systems produce ammonia from hydrogen and nitrogen. The process is mildly exothermic, with a significant reduction in the number of molecules as a result of the chemical reaction. These characteristics result in more conversion at lower temperature as well as higher pressure. The process is usually accomplished in two stages to avoid the temperature rise from a single stage and cooling is provided between the two stages. Even with these steps, the once through conversion rate for the Haber-Bosch process is usually quite low, usually less than 20%. To obtain better utilization of the feed stock (hydrogen and nitrogen) the product flow is cooled to condense out the ammonia, then reheated and returned to the inlet of the process to achieve large total conversion efficiencies. Today's system use significant energy to reheat the process flow and significant capital investment to provide the pressure capability of the reactor and heat removal capability of the increased flow through this system. At 18% once through conversion, the reactor size, the heat rejection system and the system required to reheat the process flow to the desired operating temperature are twice the size of a system that can achieve 36% once through conversion.

Today's urea production systems produce urea through the Bosch-Meiser process from a feedstock of ammonia and carbon-dioxide. The production is usually described as a two-step process, with the ammonia and carbon-dioxide first forming an ammonium-carbamate which includes one ionic bond, that ionic bond is replaced over time with a covalent bond and release of a water molecule. The ammonium-carbamate formation is mildly exothermic with a reduction in the number of molecules from three to one. As a result, very high pressures and low operating temperatures are desired to promote the product formation, with pressures in excess of 2000 psi commonly used. The ammonium-carbamate slowly converts to urea as an endothermic process with a 15-30 minute hold time usually used to achieve the urea conversion of approximately 80%. The energy needs for the ammonium-carbamate to urea conversion is usually obtained from the exothermic ammonium-carbamate formation. Although the ammonium-carbamate can be removed from the urea through the simple reduction of the pressure over the mixture, today we accomplish this removal through the reduction of the partial pressure of either the carbon-dioxide or ammonia over the mixture. This stripping process permits the released reactants to be captured and returned as input feed to the process. The urea production reactor and the ammonium-carbamate to urea hold up column are very high pressure system. In addition, the ammonium-carbamate is highly corrosive to metal because of its ionic nature. Because of this very high pressure and corrosive nature, the chemical reactor and transforming column are costly.

U.S. Pat. No. 7,645,437 describes an Integrated boiler, superheater, and decomposer for sulfuric acid decomposition for the thermo-chemical production of hydrogen. In that application we (Robert Moore, Paul Pickard, Ed Pama, Fred Gelbard, Roger Lenard and Milton Vernon) described the nesting of ceramic tubes to accomplish the chemical processing of sulfuric acid with a built in heat recovery design. That invention permitted the highly concentrated sulfuric acid to enter the unit at approximately room temperature; be heated to nearly the decomposition temperature through recovery of the sensible heat in the product discharge; be decomposed through the use of an external heat source; and then be cooled by transferring the sensible heat of the product back to the sulfuric acid reactant feed. This permitted the connections of the ceramic decomposer to be made with moderately low temperature materials, of which we had many choices. That patent described only an endothermic process utilizing one flow path for reactants and one flow path for products.

U.S. Pat. No. 5,275,632 describes a bayonet reformer in which the outside of a closed tube is heated with an externally fired source to heat the reforming reactant to produce hydrogen. This patent introduces the concept of improved combustion thermal energy recovery through the use of small gap annular combustion flow. This patent limits the improved energy performance to the improved efficiency of thermal energy recovery from combustion down to the operating temperature of the reformer, offers no thermal energy recovery of the combustion energy below the reformer temperature and provides no recovery of the reforming product sensible heat.

U.S. Pat. No. 5,429,809 describes a bayonet chemical reactor in which the outside of a closed tube is heated with a thermal fluid that raises the process reactants to the desired temperature then that fluid limits the product temperature by acting as a heat source or sink as is necessary. Although this invention limits the temperature swings within a process, it does nothing for improvement of efficiency.

U.S. Pat. No. 5,639,431 describes a bayonet reformer in which the emphasis of the patent is on removing hydrogen through the use of hydrogen permeating tubes or cylinders, in an effort to lower the operating temperature of the reformer and thus achieve some energy efficiency. This patent introduces a complicated membrane in an attempt to achieve added efficiency, but fails to address major efficiency losses such as SMR product temperature and combustion exhaust temperature.

U.S. Pat. No. 5,876,469 describes a bayonet reformer in which the emphasis of the patent is on controlling the uniformity of the heating to the pressure tubes of the reformer, which are in the bayonet design, and the recovery of the flue gas sensible heat down to the operating temperature of the reforming process. This invention fails to recover flue gas sensible heat at temperatures less than the reforming process temperature or recover any of the reforming sensible heat.

Against this background, the present invention was developed.

BRIEF SUMMARY OF THE INVENTION

Nested-flow technology is a system of flow channels developed through the nesting of circular tubes. These tubes provide a flow path bounded by the inside of an outer tube and the outside of an inner tube. The flow path is maintained open through the use of spacers within the flow path that do not substantially restrict flow. The spacing between the outer and inner tubes provides a characteristic hydraulic diameter and flow area; while the length of the tube provides a characteristic flow length.

A single nested-flow unit refers to the aggregate of all tubes nested within one another which essentially share the same axial centerline. The minimum number of nested tubes within a single nested-flow unit is determined from the number of process flows required to meet the desired result, while the maximum number of nested tubes is usually determined from other considerations such as internal pressure and material stress limits. The hydraulic diameter of flow channels can be the same or drastically different depending upon the needs of the system.

A manifold nested-flow unit refers to the assembly of multiple single nested-flow units into a common unit through the use of flow distribution manifolds. Each of the single nested-flow units performs the same process and it is the sum of these parallel operations that determine the quantitative production capability of the manifold nested-flow unit.

The nested-flow technology can be assembled into a heat exchanger by the repeated nesting of tubes one within the other, with each tube attached to a separate manifold plate at each end of the tube. A simple trade-off can be made between adding more tubes per single nested-flow unit and adding more single nested-flow units per production unit to minimize the cost of the system. The centermost tube of the single nested-flow unit can provide a flow path on the inside of the tube or not; if it provides a flow path then a final manifold plate is included to provide a corresponding flow path in the manifold assembly; if the centermost tube does not provide a flow path, the tube could be replaced by a rod and the rod or tube connected to the last manifold plate at both ends of the nested-flow tubes. For heat transfer between two fluid flows, with one fluid being heated while the other is being cooled, one flow path option is to flow the fluid being heated in one direction within all odd numbered channels, when channels are numbered from the centermost channel, while flowing the fluid being cooled in the opposite direction within all even numbered channels. For heat transfer between three fluid flows, for example say two fluids being heated and one fluid being cooled, one option is for the central most channel to be used for the first fluids being heated, the next channel out would be of the fluid being cooled and the third channel out would be of the remaining fluid being heated. This pattern would continue until all the flow channels in the single nested-flow are consumed.

The Nested-flow Technology can be assembled into a chemical reactor by the incorporation of chemical reactions sites within one or more of these nested-flow channels. Those chemical reaction sites are defined by the presence of catalyst or by the mixing of two or more fluid flows into a common volume providing an initial start point for the chemical reaction. In a single nested-flow unit the flow paths can be from one end to the other or operated as a bayonet flow with the flow returning back to the end from which it originated. These flow paths can be utilized to transfer heat, provide isolation flows for corrosion compatibility or provide resonance time for fluid flow to achieve the desired chemical conversion. A phase change jacket can be incorporated into the chemical reactor as a method of adding or removing energy at a constant temperature. Fluid can be added to the jacket at the desired temperature and state (vapor or liquid), the fluid can then change state (condense or boil) to either add energy to or remove energy from a process at a fixed temperature, then the fluid removed from the jacket in the new state. The fluid may be added or removed through a temperature gradient if the combined sensible and latent heat management is desired. A simple boiler is one example of the use of a phase change jacket which could incorporate a temperature gradient heat-up flow.

It is a primary objective of the present invention to provide a heat exchanger which is more cost effective per unit of energy transferred at the same driving temperature than we have today.

It is another objective of the present invention to provide a chemical reactor that incorporates heat transfer between the reactant and the products at a sufficiently low cost that the reactor will provide a significantly improved energy efficiency for the process.

It is another objective of the present invention to provide a chemical reactor that provides heat transfer during chemical reactions to better manage the process for improved production per product pass and reduction in non-desirable product production.

It is another objective of the present invention to provide a chemical reactor that utilizes the flow paths to limit the corrosion impact of product produced.

These and other objectives of the present invention will become apparent to those skilled in this art upon reading the accompanying description, drawings and claims.

DETAILED DESCRIPTION OF THE INVENTION

Definitions

Figure 1:
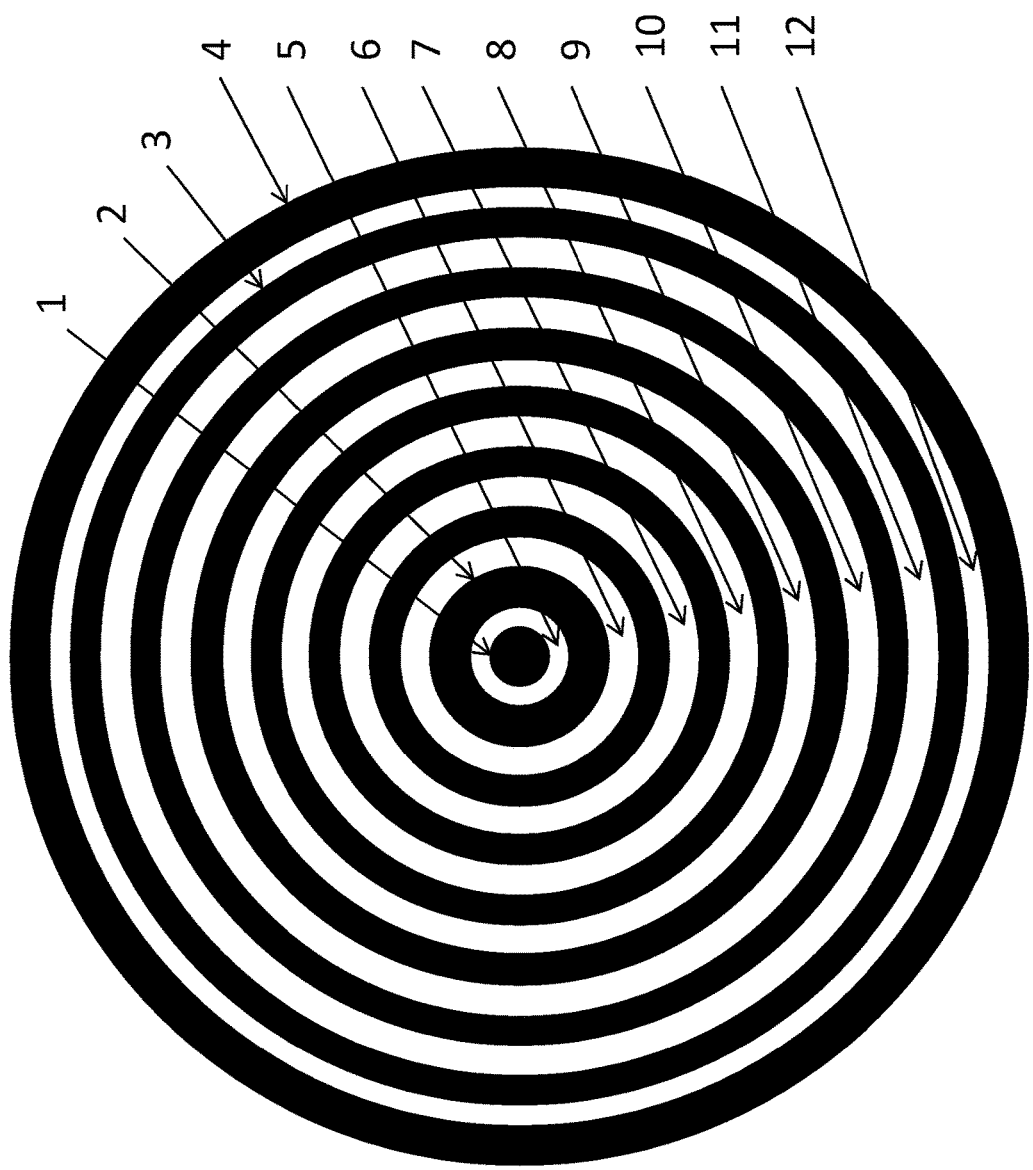
FIG. 1 is an end view of one set of nested tubes showing tubes and resulting flow channels for one design of a nested-flow heat exchanger.

Nested-flow technology as used herein shall mean a system of nested tubes with associated flow channels, created by those tubes, which are maintained as open flow channels through the use of spacers within those flow channels.

Single nested-flow unit as used herein shall mean a group of nested tubes with a common axial centerline, more or less, providing as many flow channels as desired.

Manifold nested-flow unit as used herein shall mean more than one single nested-flow unit assembled onto a common manifold for achieving desired product flow rates.

Wire wrap as used herein shall mean the installation of a small rod or wire spiraling from one end of a tube to the other end. The wire wrap can spiral fairly quickly from one end of the tube to the other, meaning that several inches of tube length would be incorporated for each wrap around the tube. The wire in this wire wrap need not be metal, but shall be compatible to the tube onto which it is wrapped and the fluid flowing within the channel in which it resides.

Phase change jacket is a larger volume enclosed by a single tube which contains a number of single nested-flow units in which the principle heat transfer mechanism is either boiling or condensation.

Endothermic process as used herein shall mean a process in which energy must be added else the reaction temperature would decrease.

Exothermic process as used herein shall mean a process in which energy must be removed else the reaction temperature would increase.

Best Mode of the Invention

Best mode of the invention as contemplated by the inventor is to maximize the energy savings within the design until the incremental energy savings from a size increase does not recover the added capital and pumping cost. As contemplated by the inventor, any tube placed within another should first have a spacer installed on the outside of the tube, and in the inventors opinion that spacer should be a "wire" spiral wrap from, essentially, one end of the tube to the other. That wire wrap should be the gap size minus any uncertainty in that gap size as a result of size uncertainties in the tubes.

How to Make the Invention

Although a single nested-flow unit can be operated, most production units will consist of a multitude of single nested-flow units connected to a common manifold system consisting of several plates, depending upon the number of flow channels in the single nested-flow unit. A plate is machined to accept the number of same size tubes needed to meet the users desired flow as well as to provide a flow path for the fluid. All nested-flow tubes of the same size are installed on the same manifold plate, and every tube size within a single nested-flow unit has an independent plate. Thus if seven size tubes are incorporated into the single nested-flow unit, then at least seven manifold plates are provide, one for each tube size. If the inner-most tube is used for a flow channel, then an eighth plate is added to provide a corresponding channel in the manifold. All tubes which go inside another are first wire wrapped to provide a physical spacer to maintain the resulting flow path open, then the tubes are attached to the manifold plates; then nested together with inclusion of catalyst, when needed, to produce a manifold nested-flow unit. The manifold can be welded, brazed, or incorporate gasket and seals to prevent loss of process fluid.

FIG. 1 shows the end view of a single set of nested tubes that can be used for a single nested-flow unit. In this arrangement, a center ⅛ inch wire wrapped rod 1 is slid into a 0.25 inch diameter 0.049 inch wall thickness wire wrapped tube 2 then six 0.035 wall thickness wire wrapped tubes each 0.125 inches larger than the other starting with a 0.375 inch tube 2 until the final 0.035 inch wall thickness 1.0 inch diameter wire wrapped tube 3. A final 1.125 inch diameter 0.049 inch wall thickness tube 4 without wire wrap is then slid over this bundle of nested tubes to provide an eight flow channel single nested-flow unit. This arrangement provides six 0.028 inch flow gaps 7, 8, 9, 10 and 11 and two 0.014 inch flow gaps 6 and 12. This nested-flow arrangement on a hexagonal configuration provides an area per volume of 850 $m^2/m^3$, rivaling the printed circuit heat exchanger area per volume at a significantly less complicated construction effort.

Figure 2:
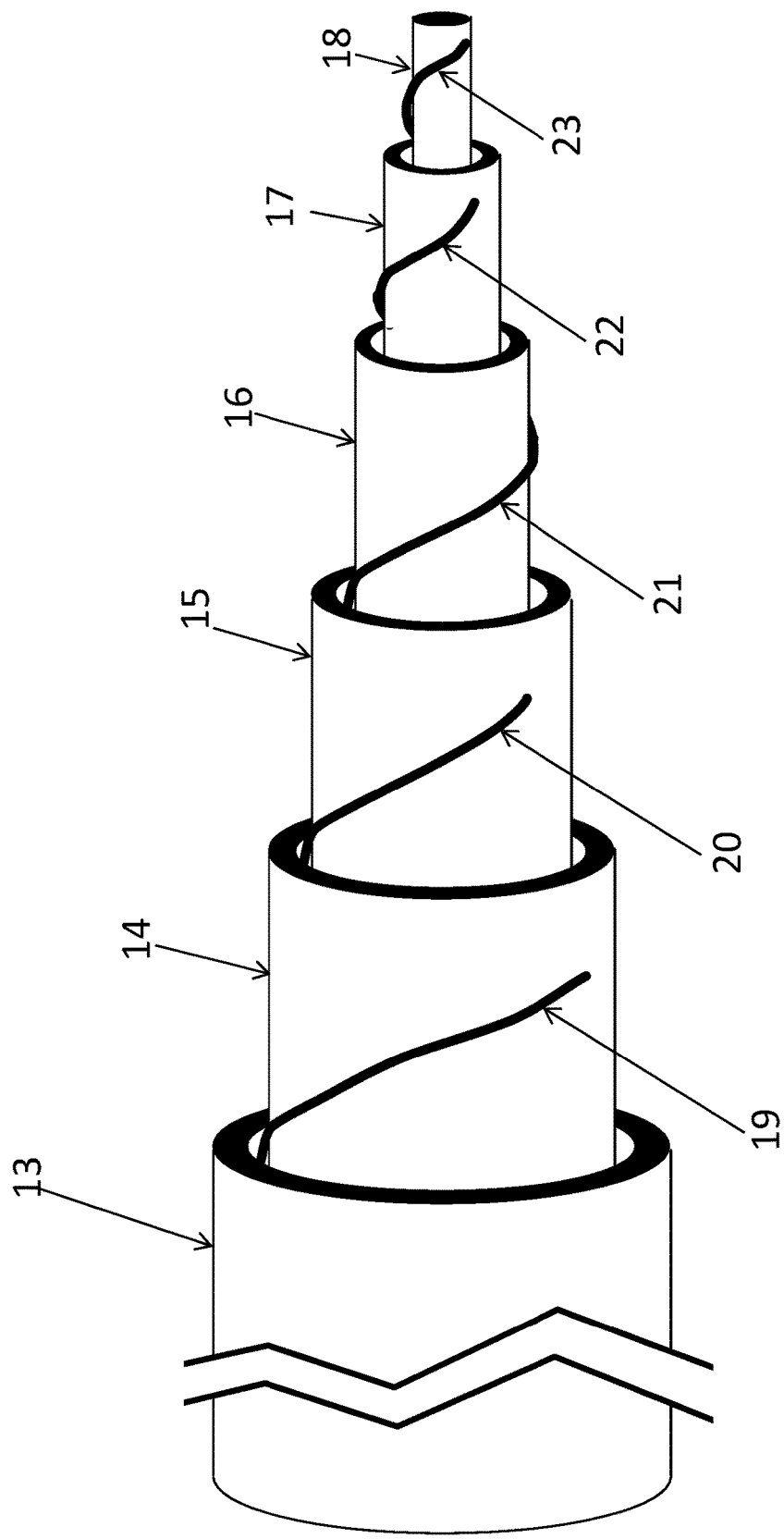
FIG. 2 is a side view of one set of nested tubes with inner tubes pulled slightly out to reveal spacers used (in this case wire wrap) to maintain flow gap spacing.

FIG. 2 shows the side view of a single set of tubes that can be used for a single nested-flow unit. Within the outer most tube 13 are nested tubes 14, 15, 16, and 17 along with a nested rod 18 each wire wrapped 19, 20, 21, 22 and 23 in order to maintain open, for fluid flow, the flow path created by the tube arrangement. While the diameters of these tubes are usually less than a few inches, the length of these tubes are several to twenty feet making the flow paths very thin and very long. These long flow paths permit the flow to reach turbulent behavior with high heat transfer effectiveness. Once in turbulent flow, the heat transfer effectiveness is nearly independent of flow rate, with only the rising pressure drop due to increasing flow that limits the performance.

Figure 3:
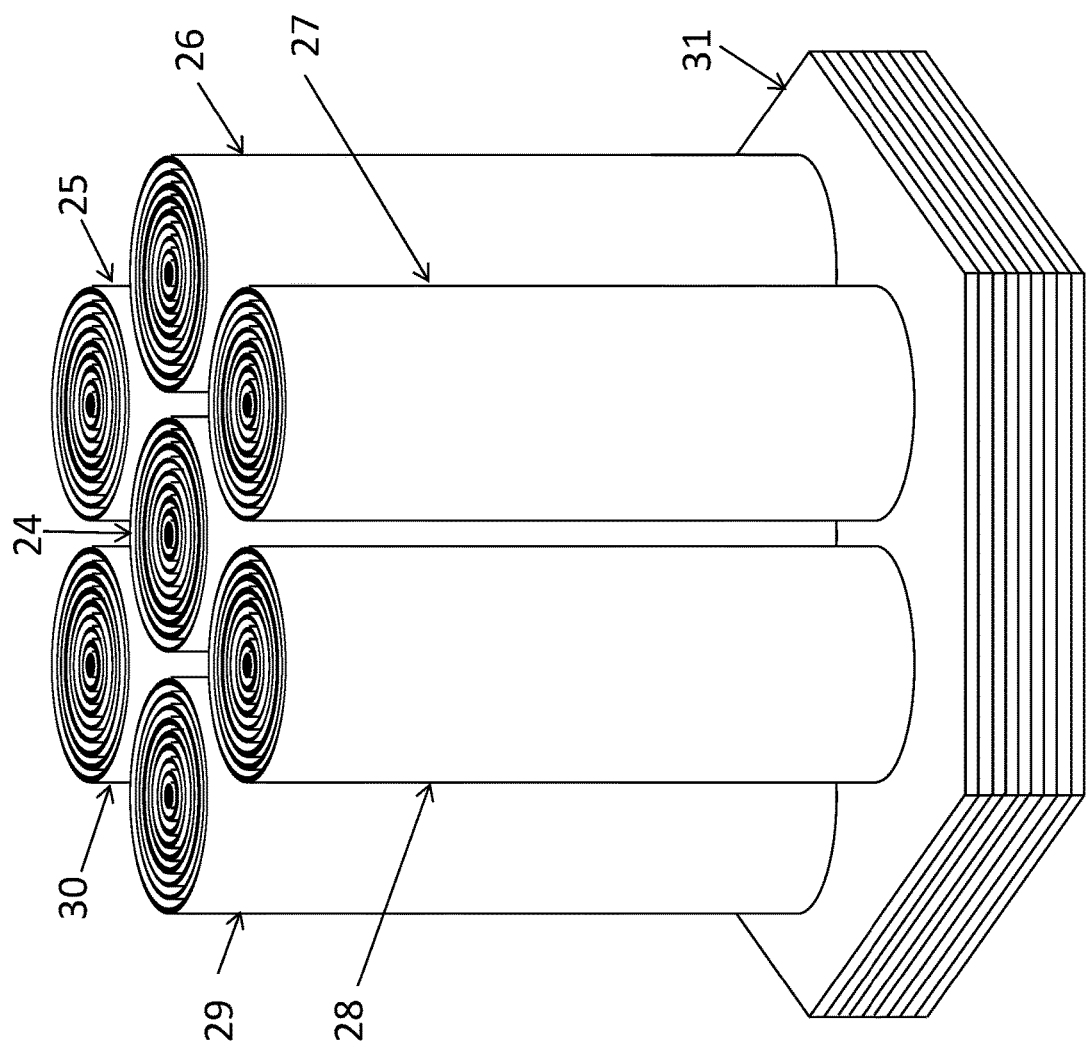
FIG. 3 is a cutaway view of a manifold nested-flow unit where seven single nested-flow units, each consisting of eight tubes and a central rod, are assembled onto one manifold.

FIG. 3 shows a cutaway view of a manifold nested-flow unit where each single nested-flow unit consists of eight nested tubes and a central rod. Seven single nested-flow units (one in the center 24 and six around that one 25, 26, 27, 28, 29 and 30) are assembled onto one manifold 31. In the nested-flow arrangement the outer tube of the nested-flow nested tubes is attached to the upper plate, the next tube in is attached to the next lower plate and so forth, until finally the rod located in the nested-flow's center is attached to the lowest plate. This manifold arrangement permits the construction of large number of single nested-flow units into a single production unit. It is only the ability to handle this manifold unit size that limits its size.

How to Use the Invention

The nested-flow technology can be used as a heat exchanger or as a chemical reactor or as a combined unit accomplishing both chemical reaction and heat exchange.

FIG. 3 shows the basic configuration of the nested-flow technology attached to one manifold using seven single nested-flows units, each consisting of one rod and eight tubes. This arrangement provides eight flow paths. When used as a two flow heat exchanger a similar manifold is installed at the other end of the tubes and every other flow path is used for one fluid flow and the remaining paths serve the remaining fluid flow.

Examples of the Invention

Figure 4:
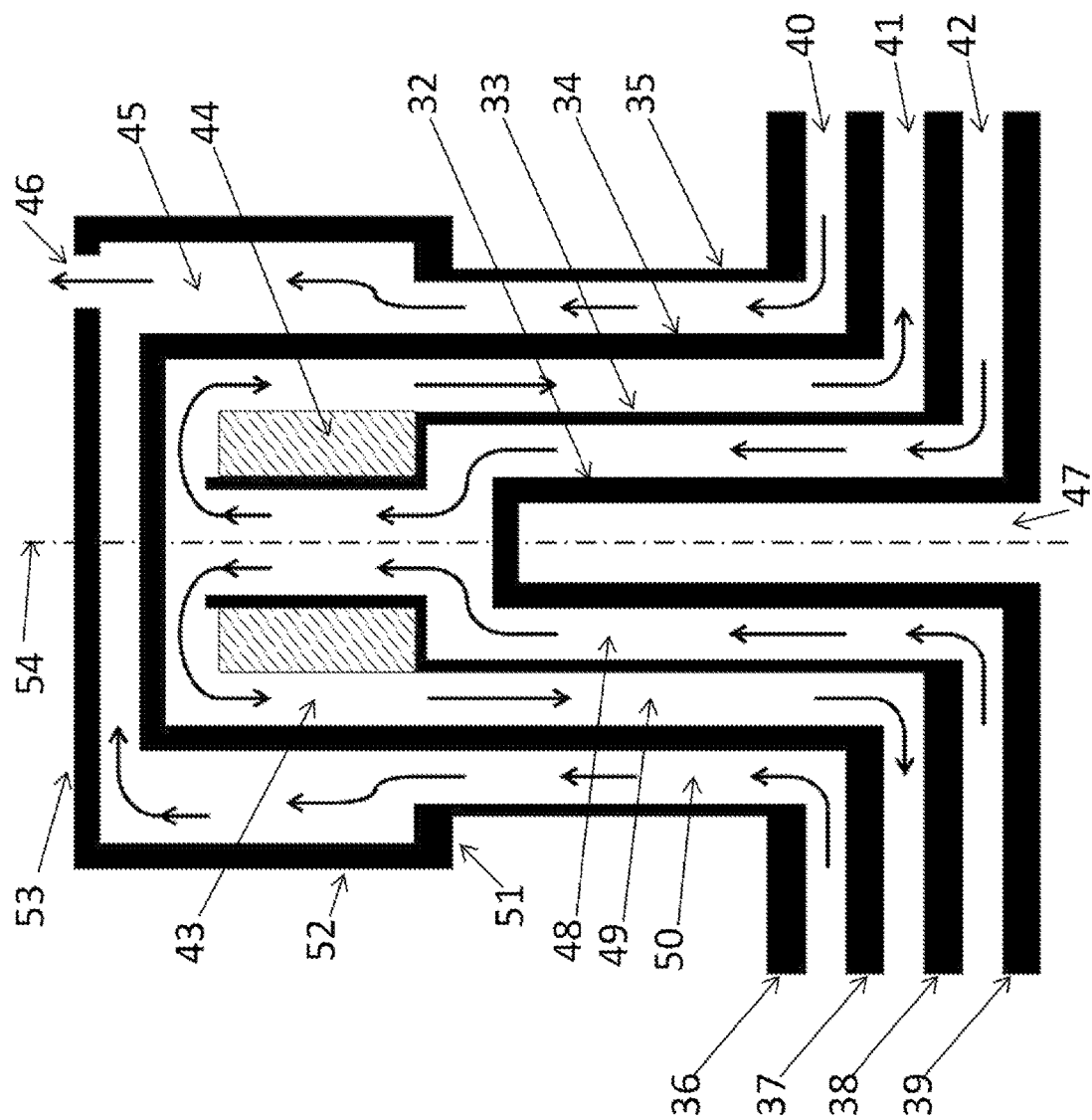
FIG. 4 is a cutaway view of a single nested-flow unit used for ammonia production.

FIG. 4 shows a cutaway view of a single nested-flow unit used for ammonia production. Reference centerline 54 is shown as a reminder that the configuration is a set of nested tubes where the created flow paths are maintained through the use of a widely spaced spiral "wire" wraps. Ammonia is produced when the nitrogen and hydrogen reactants are heated to an optimum temperature and exposed to a formation catalyst. That optimum temperature is a tradeoff driven by the speed of formation which favors higher temperatures and extent of conversion favored by lower temperatures. In the nested-flow unit, the energy to raise the reactant flow to the optimum temperature is obtained from the product flow. Innermost tube 32 is used to reduce the gap in the reactant channel 48 created by the outside surface of tube 32 and the inside surface of tube 33 to improve this heat transfer. Tube 32 is a relatively small diameter tube, approximately 0.5 inches+/−0.25 inches in diameter but extends many feet into the nested-flow where it is sealed with an end plug. The length of tube 32 is driven by the need for heat transfer area. Cavity 47 provides a volume for thermal couple insertion for chemical reactor control if so desired. Tube 32 is attached to manifold plate 39 and manifold plate 39 may have many similar tubes attached, one for each single nested-flow unit in the final manifold nested-flow unit, all having a common reactant input 42. Tube 33 is used as a flow baffle to force the flow from the cooler end of this unit to the warmer end and then back to the cooler end. Tube 33 becomes the outer boundary of the reactant channel and the inner boundary of the product channel 49. Tube 33 is attached to manifold plate 38, which may have many similar tubes attached, one for each single nested-flow unit in the final manifold nested-flow unit, all having a common product outlet 41. Tube 33 is approximately 0.625 inches+/−0.25 inches in diameter between the manifold connection and past tube 32, where its diameter is reduced to permit the placement of an ammonia production catalyst 44. Tube 33 is not closed at the upper end, but left open permitting the reactants to flow from the inside of tube 33 to the outside at the warmer end of the nested-flow system. Tube 33 provides the heat transfer surface area for the for the thermal energy exchange between the reactants in channel 48 and the products in channel 49. Tube 34 provides the outer surface of the product flow channel. Tube 34 is attached to manifold plate 37, which may have many similar tubes attached. Tube 34 is approximately 0.75 inches+/−0.25 inches and ten to twenty feet long. Tube 34 is closed at the warm end of the nested-flow, forcing the reactants to flow across the catalyst and form ammonia which is then cooled as it flows towards the cooler end of the nested-flow by both the reactant flow 48 and the water jacket flow 50. Tube 35 provides an outer boundary for the cooling jacket water flow. Tube 35 is attached to manifold plate 36, which may have many similar tubes attached. Manifold plate 36 provides for a common water input 40 for all of the single nested-flow units installed in the manifold nested-flow unit. Tube 35 is approximately 0.875 inches+/−0.25 inches in diameter, and runs from manifold plate 36 to an intermediate manifold plate 51 just before the catalyst region of this nested-flow system. Manifold plate 51 is a transitional manifold plate which goes from one tube around each nested-flow to a common tube 52 around all nested-flow units attached to manifold 36. This common tube 52 provides a boiling region 45 for all single nested-flow units that allow the system to be operated either vertically or horizontally. Tube 52 is approximately 2 ft+/−1 ft in diameter and 2 ft+/−1 ft in length. A pressure vessel end cap 53 is attached to tube 52, with an exit port 46 near the top of the unit, which depends on the orientation, for steam to be used elsewhere in the production operation. This steam removes nearly all of the heat of formation for the ammonia operation. A manifold nested-flow unit for the production of twenty metric tons per day at a per cycle conversion fraction of 17% would be approximately one foot in diameter and ten feet long. The nested-flow design for ammonia production converts an ammonia production process from an energy consumption process costing $12/ton-of-ammonia to an energy production process worth $12/ton-of-ammonia based on natural gas cost of $4/million-BTUs.

Operation of the ammonia manifold nested-flow unit is accomplished by first heating the water in region 45 to the operation temperature for the water. The reactant mixture of approximately one molar part nitrogen and three molar parts hydrogen is introduced at the common port 42. The reactants are heated by the tube surfaces as they flow toward the warm end of the nested-flow, where they form ammonia when in contact with the catalyst 44. Most of the heat of formation is deposited in the common boiling water volume 45, where the steam produced is removed for use elsewhere. The ammonia and un-reacted hydrogen and nitrogen are cooled as they move towards the cooler end of the nested-flow, providing the heat to the tubes which is used to heat both the reactants and water to their desired temperature. The flow from all the nested-flows is gathered inside the manifold where it exits at the common port 41. The ammonia will condense as it is cooled in flow channel 49. If operated vertically, then the ammonia, nitrogen and hydrogen are separated shortly after exiting the nested-flow manifold. If operated horizontally, then a lower and upper port can be incorporated for port 41, permitting separation of ammonia from un-reacted reactants within the manifold. Significantly higher once through production rates will occur because the temperature is not permitted to rise in the production of ammonia. As a result, significantly less recycling will occur and the total ammonia production size will be smaller.

Figure 5:
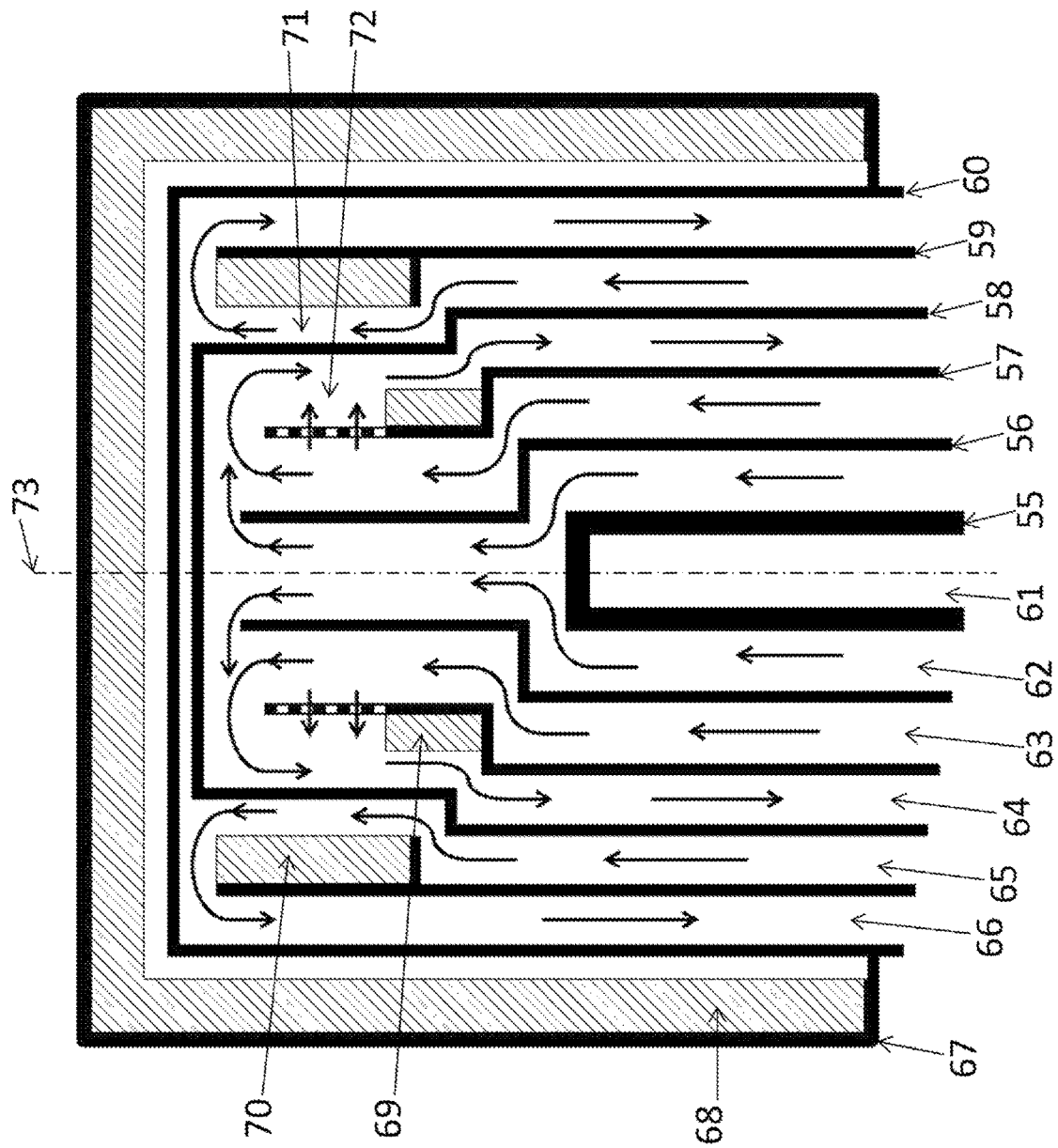
FIG. 5 is a cutaway view of a single nested-flow unit used for Steam Methane Reforming.

FIG. 5 shows a cutaway view of a single nested-flow used for Steam Methane Reforming (SMR). Centerline 73 is added to remind the reader that the nested-flow consists of a series of nested tubes with a more-or-less common centerline. Steam Methane Reforming is a process where steam and methane are reacted at relatively high temperatures to produce carbon-monoxide and hydrogen. The center most tube 55 is used to reduce the gap of the methane used as a combustion heat source that drives the endothermic SMR process and provides a cavity 61 for the insertion of one or more thermocouples for process controls if so desired. Wire wrap tube 55 has a diameter of approximately 0.5 inches+/−0.25 inches and is 8 feet to 18 feet long. Wire wrap tube 56 has a diameter of approximately 0.625 inches+/−0.25 inches, and provides the outer surface of the combustion methane flow channel 62 and the inner surface of the combustion air flow channel 63. The combustion reactants are maintained in separate channels due to the tendency to auto-ignite prior to arriving at the desire combustion location 72. Wire wrap tube 57 has a diameter of approximately 0.75 inches+/−0.25 inches, and provides the outer surface of the combustion air channel and the inner surface of the combustion exhaust channel 64. Wire wrap tube 58 has a diameter of 0.875 inches+/−0.25 inches and provides the outer surface of the combustion exhaust channel and the inner surface of the SMR reactant channel 65. Tube 58 is plugged at the warm end of the assembly to force the air and methane of the combustion process to start flowing down the tube where the combustion process occurs. Wire wrap tube 59 has a diameter of 1.0 inches+/−0.25 inches and provides the outer surface of the SMR reactant flow channel and the inner channel of the SMR product flow channel 66. Tube 60 has a diameter of 1.125 inches+/−0.25 inches and provides the outer surface of the SMR products. Tube 60 is plugged at the warm end of the tube and is the outer tube of the nested-flow tubes. All of the single nested-flows units that are assembled for a manifold nested-flow unit are housed within a common pressure tube 67. Tube 67 has a thermal insulator blanket 68 that isolates tube 67 form the internal temperatures of the nested-flow units, allowing the use of stainless steel throughout the system by minimizing the pressure differential across all tubes with the exception of tube 67.

The methane flow for combustion is through channel 62. This methane flow is heated as it moves toward the warm end of the nested-flow nested tubes. The air flow for combustion is through channel 63. This air flow is heated as it moves toward the warm end of the nested-flow nested tubes. The methane and air are mixed at the warm end of the nested-flow unit, where the temperatures are greater than 800° C. Since the auto-ignition temperature for methane air is approximately 550° C., the methane and air will auto-ignite. The reactant flow for the SMR process is a mixture of steam and methane introduced through channel 65. The SMR reactant flow is heated as it travels toward the warm end of the nested-flow nested tubes, but will not substantially react until it enters the SMR catalyst 70 region of the channel 71. The SMR process has a significant entropy gain, going from three molecules of reactants to four molecules of products and proceeds nearly to completion provided sufficient energy is provided through the combustion process occurring in region 72. By having the combustion process so tightly coupled with the SMR process, the combustion process is only a few degrees hotter than the SMR process. As a result, the methane combustion process of the nested-flow system will have an equilibrium level significantly higher than 85% combustion level of the standard 2000° C. methane combustion. In addition, a combustion catalyst 69 is included in the system to take the methane combustion to even higher values as the combustion gases cool from loss of energy to the SMR process. Assembled into a manifold nested-flow unit, the SMR production unit will be twenty feet long and approximately twenty inches in diameter to meet the hydrogen production needs for twenty tons of ammonia per day. The efficiency improvement provided by the nested-flow technology will reduce the cost of hydrogen production from $140/ton-of-ammonia to $110/ton-of-ammonia based on natural gas cost of $4/million-BTUs.

Figure 6:
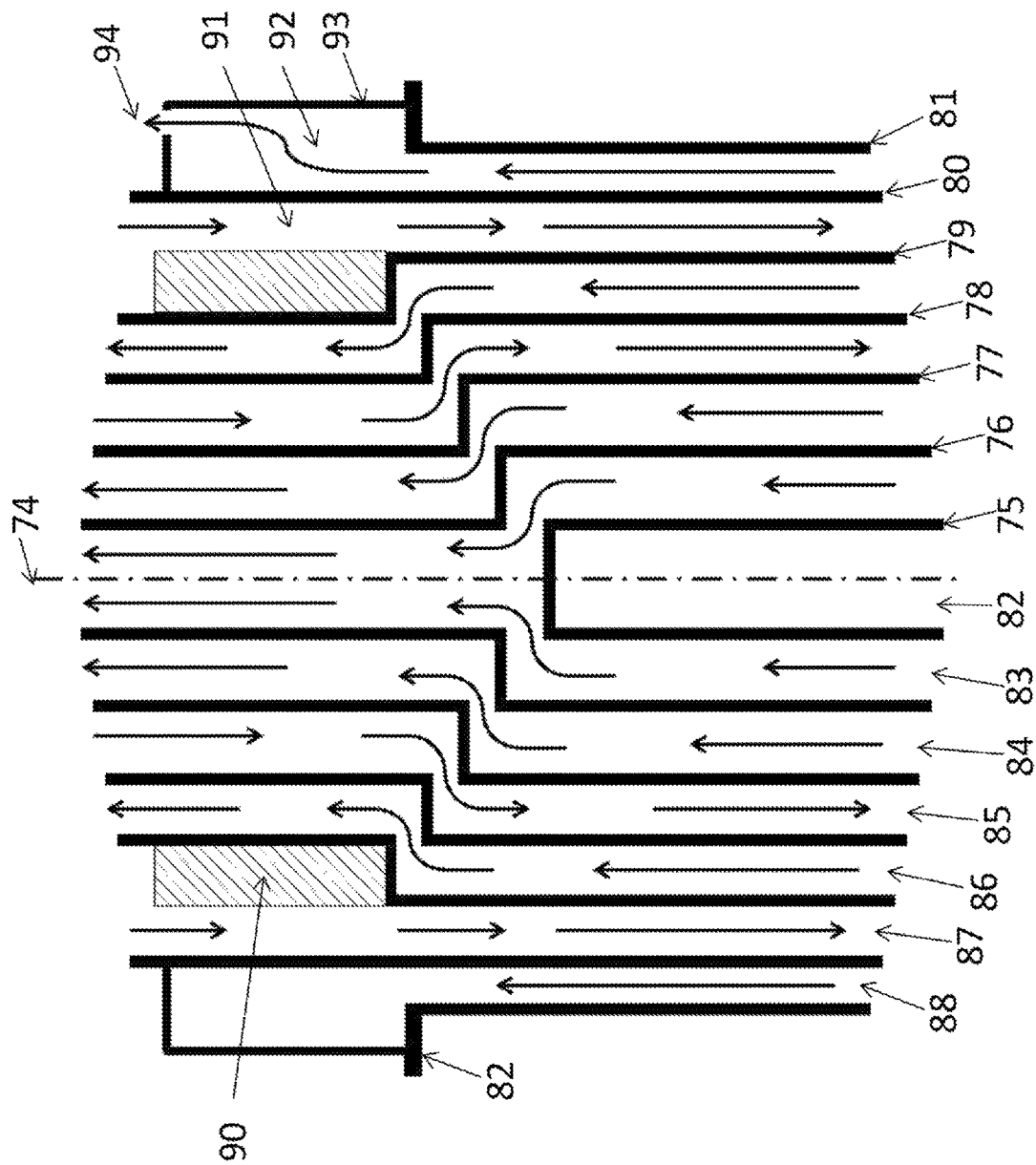
FIG. 6 is a cutaway view of a single nested-flow unit used for Water Shift Reaction.

FIG. 6 shows a cutaway view of a single nested-flow used for Water Shift Reaction (WSR). Centerline 74 is added to remind the reader that the nested-flow consists of a series of nested tubes with a more-or-less common centerline. The WSR is a mildly exothermic process in which one mole of carbon-monoxide and one mole of water is reacted to produce one mole of carbon-dioxide and one mole of hydrogen. The optimum reaction temperature is a tradeoff driven by the speed of formation which favors higher temperatures and extent of conversion favored by lower temperatures. This WSR unit also serves to preheat the reactants for the SMR process and cool the products from the SMR to a lower temperature. This recuperation heat exchanger is built into the nested-tube arrangement of the WSR to same space. One option for the WSR unit is to incorporate it into the SMR unit producing a combined SMR/WSR unit. For clarity, these two units are shown separately. Wire wrapped tube 75 serves to improve the heat transfer between flows by decreasing the gaps in outer nested-flows. Wire wrapped tube 76 serves as a separation barrier between the combustion methane flow 83 and combustion air flow 84. Wire wrapped tube 77 serves as a separation barrier between the combustion air flow and the combustion exhaust product flow 85. It is the surface area of this tube and the hydraulic diameters of the adjacent flow channels that determine the temperature difference between these two flows. Wire wrap tube 78 serves as the barrier between the combustion exhaust flow and the WSR/SMR reactant flow 86. It is the heat transfer area of this tube and the hydraulic diameter of channels 86 and 87 that are the hardware drivers for determining the temperature difference between these two flows. Wire wrapped tube 79 serves as the barrier between the WSR/SMR reactant flow 86 and the WSR/SMR product flow 87. Wire wrapped tube 80 serves as the barrier between the WSR/SMR product flow 87 and the water cooling jacket flow 86 which removes the excess heat from the WSR process. The SMR products and excess water flow down channel 87 where they react when in contact with catalyst 90 in region 91. The length of catalyst 90 is determined from both the catalyst resonance time requirement and channel 87 flow rates. Tube 81 serves as the outer channel barrier for the coolant channel 88, tube 81runs from the lower manifold (not shown) to an intermediate manifold 82. The intermediate manifold is a transition plate to allow the water flow channel 88 from all the nested-flow units to enter into a common volume 92 for water boiling, which is bounded by the larger circular tube 93. This common boiling volume permits the operation of the unit in either a horizontal or vertical orientation; exit 94 is provided at the top of this volume based upon that orientation. The WSR nested-flow system is similar in layout to the SMR nested-flow system, with the exception that the WSR nested-flow system results in all flows going through the unit while the SMR nested-flow system had all flows in the bayonet configuration. Assembled into a manifold nested-flow unit, the WSR production unit will be ten feet long and approximately twenty inches in diameter to meet the hydrogen production needs for twenty tons of ammonia per day. The efficiency improvement provided by the nested-flow technology will change the process energy needs from a process that requires external steam production at a cost of approximately $2.30/ton-of-ammonia to a process that is nearly self-sufficient in generating its own steam based on natural gas cost of $4/million-BTUs.

Figure 7:
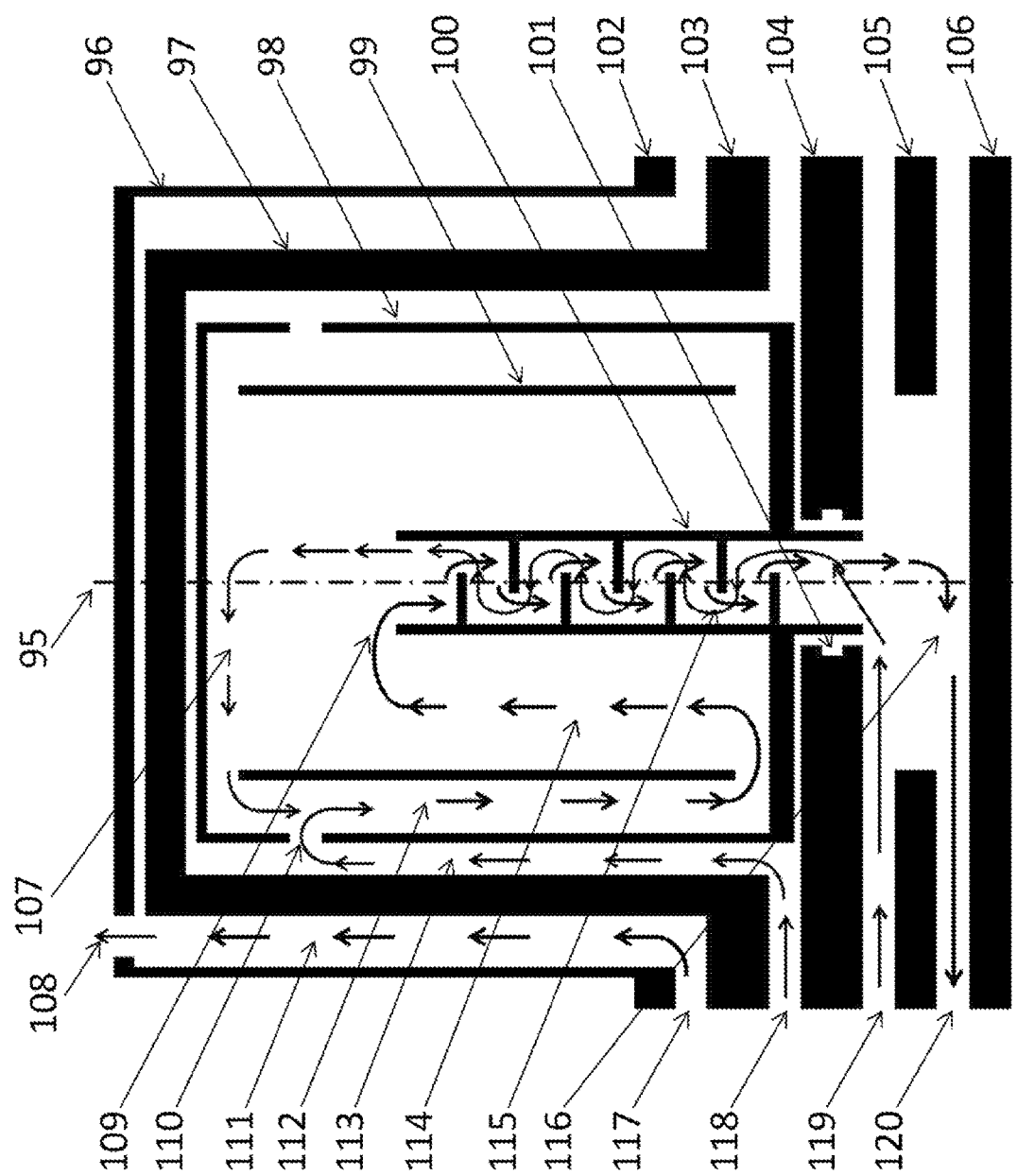
FIG. 7 is a cutaway view of a single nested-flow used for urea production.

FIG. 7 is a cutaway view of a single nested-flow used for urea production. Centerline 95 is included to remind the reader that the nested-flow is a nested tube assembly. Urea is produced by combining carbon-dioxide with ammonia at high pressure and slightly elevated temperatures. Tube 96 is the pressure boundary of a boiling volume used to control the operating temperature of the urea formation process. The pressure within volume 111 is regulated to control the boiling temperature. Tube 96 is approximately two feet in diameter and encloses all of the single nested-flow unit for urea production. For non-portable plants, this tube could be up to twenty feet long, while for portable plants, this tube may be as short as six feet long. Tube 97 is approximately 3 to 4 inches in diameter and is the outer tube and pressure boundary of the single nested-flow unit. The nested-flow unit length is dependent upon site constraints and could be as short as six feet or as long as twenty feet. Tube 97 is constructed of thick walled stainless steel for pressure requirements. "Wire" wrapped tube 98 and all tubes nested within tube 98 are non-metallic to provide compatibility with the ammonia-carbamate being formed in the down-flow channel 112. "Wire" wrapped tube 99 provides an initial formation channel for the ammonia-carbamate which is only slightly more dense than water. The ammonia-carbamate flows to the lower end of channel 112, and then flows up between tube 99 and tube 100. Tube 100 is a tube with many cascading ledges to slow the fall of the urea/ammonia-carbamate mixture as this mixture flow down the tube. O-ring grove 101 provides one method of sealing the non-metallic nested tubes to the manifold plates. Manifold plate 102 provides the upper flow path for the boiling flow 117 that cools all the single nested-flow units within this manifold nested-flow unit. Plate 103 serves as the lower boundary for that boiling flow and the upper boundary for one of the urea reactants flow, carbon-dioxide. Plate 104 serves as the lower boundary for that reactant flow and the upper plate of the remaining reactant flow, ammonia. Plate 105 serves as the lower boundary for the second reactant flow and the upper plate of the urea discharge flow. Plate 106 serves as the lower plate for the urea discharge flow. Flow 117 is the liquid flow into the common boiling region 111, while flow 108 is the gaseous discharge from that region. Flow 118 is the common flow of the reactant, carbon-dioxide. This reactant flow through nested-flow channel 113, providing a sweep gas to assure no ammonia-carbamate enters this channel and corrodes the pressure boundary provided by tube 97. At location 110, the carbon-dioxide gas enters the non-metallic flow channel 112 where it reacts with the ammonia reactant and forms ammonia-carbamate. This ammonia-carbamate flows down channel 112 then up channel 114, providing sufficient resonance time to convert approximately 80% of the ammonia-carbamate into urea. The urea/ammonia-carbamate mixture then spills over tube 100 at the upper end 109 and cascades down a series of landings to permit the ammonia reactant flow to strip the urea of ammonia-carbamate by subjecting the mixture to a constantly decreasing carbon-dioxide partial pressure. This stripping action results in extremely low levels of ammonia-carbamate in the urea flow at the lower end of tube 100. All single nested-flow units combine their urea flow into manifold channel 120 where it is discharged from the production unit. Flow channel 119 provides the common entrance point for ammonia. Ammonia reactant is used as a stripping gas to remove the ammonia-carbamate from the down-flowing liquid mixture. Ammonia is used as the stripping gas to suppress the formation of Biuret, a chemical that is damaging to some crops. At region 116, the carbon-dioxide vapor pressure is essentially zero, while the vapor pressure of the ammonia is essentially the operating pressure of the urea production system. This ammonia flows counter to the urea/ammonia-carbamate mixture, the mixture being a liquid and the reactant being a gas. As the reactant flow moves up tube 100, the vapor pressure of the carbon-dioxide increases due to the decomposition of the ammonia-carbamate as a direct result of the reduced carbon-dioxide partial pressure. Eventually the ammonia reactant flow 107 exits the top of tube 100 carrying with it all of the carbon-dioxide and ammonia released from the decomposition of ammonia-carbamate from this liquid/gas counter-flow stripping reaction. All of this gas flow is then mixed with the feed carbon-dioxide reactant flow in channel 112 where the deficiency in the carbon-dioxide partial pressure is made up by the feed of carbon-dioxide reactant flow through opening 110 and ammonia-carbamate once again is formed. Configured as 6 ft tall columns, a total of 110 columns will be required to obtain a resonance time of approximately 20 minutes. One arrangement could be three units each 24 inches in diameter and 80 inches tall. This urea production nested-flow system provides a compact and economic system for the ammonia-carbamate formation, urea formation and stripping step for removing residual ammonia-carbamate form the urea.

Deployment of the Invention

These chemical reactors permit the modularization of a fertilizer plant. One modularization option would be to house these chemical reactors into standard forty feet long eight feet wide and eight feet tall shipping containers. To meet production goals of thirty-five tons per day of urea, only two shipping containers would be required to house all the chemical reactors, purification equipment, pumps and compressors. Such an arrangement would permit the equipment to be deployed rapidly to both regions that are short of fertilizer production capability and locations where natural gas is being wasted through flaring operations. For locations that are not supported or under-supported with electrical power, hydrogen production can be increased to provide additional hydrogen for use in hydrogen based fuel cells for production of needed electrical power. To meet 20 tons/day ammonia or 35 tons/day urea production, 1½ million cubic feet per day of hydrogen measured at STP will be required. If the hydrogen production is doubled, a 35 ton/day urea production plant could provide approximately 3.5 MW of electrical power using hydrogen fuel cell technology.

What is claimed is:

1. A chemical reactor comprising:
    a first tube;
    a second tube positioned in the first tube and defining an annular space between the first tube and the second tube; and
    a manifold assembly coupled to a first end of the first tube and a first end of the second tube, wherein the manifold assembly defines a first opening in direct fluid communication with the annular space between the first tube and the second tube and a second opening in direct fluid communication with a channel along the length of the second tube,
    wherein a second end of the second tube is open proximate a second end of the first tube.

2. The chemical reactor of claim 1, wherein the first tube and the second tube are coaxial.

3. The chemical reactor of claim 1, wherein a bayonet flow path is defined by the annular space, the first and second openings, and the channel, and comprising a catalyst disposed along the bayonet flow path.

4. The chemical reactor of claim 1, comprising a heating assembly disposed around the manifold assembly.

5. The chemical reactor of claim 1, comprising a water shift reaction (WSR) unit configured to receive a product gas generated in the chemical reactor.

6. The chemical reactor of claim 1, wherein a length of each of the first tube and the second tube is at least 10 feet.

7. The chemical reactor of claim 1, wherein the first tube is formed of a metal.

8. The chemical reactor of claim 1, wherein the second tube is formed of a metal.

9. A method comprising:
    flowing a gas along a bayonet flow path of a chemical reactor, the bayonet flow path being defined by:
        an annular space defined between a first tube and a second tube positioned in the first tube;
        a channel along the length of the second tube;
        a first opening defined in a manifold assembly coupled to a first end of the first tube and a first end of the second tube, wherein the first opening is in direct fluid communication with the annular space between the first tube and the second tube; and
        a second opening defined in the manifold assembly, wherein the second opening is in direct fluid communication with the channel along the length of the second tube.

10. The method of claim 9, comprising exchanging heat between gas flowing in the annular space and gas flowing in the channel along the length of the second tube.

11. The method of claim 9, in which flowing a gas along a bayonet flow path comprises flowing the gas in a first direction in the annular space and flowing the gas in a second direction opposite the first direction in the channel along the length of the second tube.

12. The method of claim 9, comprising producing hydrogen, in the chemical reactor, from the gas flowing along the bayonet flow path.

13. The method of claim 9, in which flowing a gas along a bayonet flow path comprises flowing a gas containing steam and methane.

14. The method of claim 13, comprising reacting the steam and the methane along the bayonet flow path to produce hydrogen and carbon monoxide.

15. The method of claim 9, comprising exposing the flowing gas to a catalyst disposed along the bayonet flow path.

16. The method of claim 9, wherein a temperature of the flowing gas in the manifold assembly is higher than a temperature of the flowing gas at the first end of the first tube.

17. The method of claim 16, wherein a temperature in the chemical reactor at the manifold assembly is greater than 800° C.

18. The method of claim 9, comprising heating the flowing gas in the manifold assembly using heat generated by combustion.

19. The method of claim 9, in which flowing a gas along a bayonet flow path comprises flowing the gas in turbulent flow along at least a portion of the bayonet flow path.

20. The method of claim 9, comprising cooling a product gas generated in the chemical reactor in a WSR unit.

21. The method of claim 20, comprising producing hydrogen and carbon dioxide in the WSR unit.

* * * * *